(12) United States Patent
Hou et al.

(10) Patent No.: US 9,139,502 B2
(45) Date of Patent: Sep. 22, 2015

(54) USE OF AN URUSHIOL COMPOUND IN PREPARATION OF PHARMACEUTICAL COMPOSITIONS FOR INHIBITING SMAD3 PHOSPHORYLATION

(71) Applicants: Southern Hospital, Southern Medical University, Guangzhou (CN); Kunming Institute of Botany, Chinese Academy of Sciences, Kunming (CN)

(72) Inventors: Fan Fan Hou, Guangzhou (CN); Yongxian Cheng, Kunming (CN); Jing Nie, Guangzhou (CN); Jun Al, Guangzhou (CN); Jiangbo He, Kunming (CN)

(73) Assignees: SOUTHERN HOSPITAL, SOUTHERN MEDICAL UNIVERSITY, Guangzhou (CN); KUNMING INSTITUTE OF BOTANY, CHINESE ACADEMY OF SCIENCES, Kunming (CN)

( * ) Notice: Subject to any disclaimer, the term of this patent is extended or adjusted under 35 U.S.C. 154(b) by 0 days.

(21) Appl. No.: 14/531,309

(22) Filed: Nov. 3, 2014

(65) Prior Publication Data
US 2015/0175511 A1    Jun. 25, 2015

(30) Foreign Application Priority Data
Nov. 4, 2013    (CN) .......................... 2013 1 0539667

(51) Int. Cl.
C07C 39/19    (2006.01)
A61K 31/05    (2006.01)

(52) U.S. Cl.
CPC ................. *C07C 39/19* (2013.01); *A61K 31/05* (2013.01)

(58) Field of Classification Search
None
See application file for complete search history.

(56) References Cited

FOREIGN PATENT DOCUMENTS

| CN | 101805246 A | 8/2010 |
|---|---|---|
| CN | 103371986 A | 10/2013 |
| CN | 103371987 A | 10/2013 |

OTHER PUBLICATIONS

Database CAPLUS in STN, Acc. No. 2010:1052726, Cheng et al., CN 101805246 A (Aug. 18, 2010) (abstract).*

* cited by examiner

*Primary Examiner* — Brian J Davis
(74) *Attorney, Agent, or Firm* — Vic Lin; Innovation Capital Law Group, LLP

(57) ABSTRACT

The invention relates to a use of an urushiol compound (code named GQ-5) in preparation of pharmaceutical compositions for inhibiting Smad3 phosphorylation. We verify that GQ-5 inhibited the interaction of Smad3 with TGF-β type I receptor (TβRI), inhibited subsequent phosphorylation of Smad3, reduced nuclear translocation of Smads complex, and suppressed the transcription of major fibrotic genes such as α-smooth muscle actin (α-SMA), collagen I and fibronectin. Therefore, GQ-5 could be a potent and selective inhibitor of TGF-β1-induced Smad3 phosphorylation, and be used to prepare pharmaceutical compositions for inhibiting Smad3 phosphorylation.

1 Claim, 18 Drawing Sheets

| position | δ H (ppm, J in Hz) | δ C |
|---|---|---|
| 1 | | 142.9 |
| 2 | | 141.8 |
| 3 | | 129.4 |
| 4 | 6.72, m | 122.1 |
| 5 | 6.72, m | 120.1 |
| 6 | 6.72, m | 112.8 |
| 1' | 2.61, t (7.5) | 29.0 |
| 2' | 1.62, m | 29.2 |
| 3'–6' | 1.32, m | 29.5 |
| 7' | 2.04, m | 27.2 |
| 8' | 5.37, m | 129.8 |
| 9' | 5.37, m | 129.9 |
| 10' | 2.04, m | 27.2 |
| 11' | 1.32, m | 29.5 |
| 12' | 1.32, m | 29.5 |
| 13' | 1.32, m | 31.8 |
| 14' | 1.32, m | 22.6 |
| 15' | 0.90, t (7.0) | 14.1 |

USE OF AN URUSHIOL COMPOUND IN PREPARATION OF PHARMACEUTICAL COMPOSITIONS FOR INHIBITING SMAD3 PHOSPHORYLATION

FIELD OF THE INVENTION

This invention relates to a novel use of an urushiol compound isolated from *Resina Toxicodendri*, and in particular, to a use of an urushiol compound in preparation of pharmaceutical compositions for inhibiting Smad3 phosphorylation.

BACKGROUND OF THE INVENTION

Natural pharmaceuticals play an important role in the research of the field of medical care and pharmaceutical research. It is shown that 80% of antimicrobial drugs and 60% anticancer drugs originate directly or indirectly from natural products (*J Nat Prod*, 2003, 66: 1022-1237).

*Resina Toxicodendri* is the dried resin secreted by *Toxicodendron vernicifluum* and has been used as an anti-inflammatory and anti-scarring agent in traditional Chinese medicine for centuries.

Chinese patent application no. 201010149042.3, titled "Urushiol compound and medicinal composition thereof, preparation method and application" thereof, filed on Apr. 16, 2010, published on Aug. 18, 2010 with publication no. CN101805246A, granted on Jun. 5, 2013, disclosed that the researchers of Kunming Institute of Botany, Chinese Academy of Sciences (Kunming, China) isolated and purified an urushiol compound with the following structural formula:

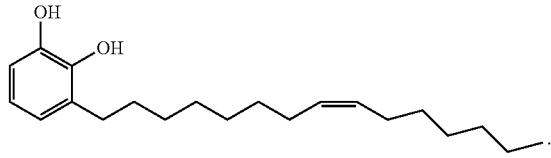 [SMILES: CCCCCC/C=C\CCCCCCCc1cccc(O)c1O]

The above urushiol compound is marked with a code GQ-5. GQ-5 is a small molecular urushiol compound with a molecular formula, $C_{21}H_{34}O_2$. The compound preparation formed by the urushiol compound has obvious effects of inhibiting tumor cytotoxin activity and tumor angiogenesis.

Inventors of the present invention, from Southern Medical University (Guangzhou, China) continue the research of the phenolic component GQ-5 has effective of inhibiting fibrosis of liver tissue and kidney tissue. They filed the following two Chinese patent applications: CN 201010149042.3, titled "Use of an urushiol compound in preparation of drug for inhibiting fibrosis of liver tissue", filed on Apr. 17, 2012, published on Oct. 30, 2013 with publication no. CN103371986A; CN 201210111642.X, titled "Use of an urushiol compound in preparation of drug for inhibiting fibrosis of kidney tissue", filed on Apr. 17, 2012, published on Oct. 30, 2013 with publication no. CN103371987A.

All patents, patent publications, and non-patent publications cited are incorporated by reference herein.

TGF-β1 signals are transduced by transmembrane serinethreonine kinase receptors type I (TβRI) and type II (TβRII) and intracellular mediators known as Smads. Upon TGF-β1 stimulation, Smad2 and Smad3 are phosphorylated by TβRI. Phosphorylated Smads heterooligomerize with the common partner Smad4 and then translocate into the nucleus, where they control the transcription of TGF-β-responsive genes through interaction with specific cis-acting elements in the regulatory regions. Although both Smad2 and Smad3 are strongly activated in various experimental and human fibrotic kidney diseases, it is now well recognized that Smad3 is the key mediator of TGF-β1-induced ECM production and tissue fibrosis. Deletion of Smad3 suppresses fibrogenesis in a number of rodent models, including diabetic nephropathy, obstructive nephropathy, and drug toxicity-related nephropathy. On the other hand, conditional knocking out of Smad2 from kidney tubular cells significantly enhanced renal fibrosis via up-regulation of Smad3 signaling. These findings indicate that Smad3 expression and/or phosphorylation might be a potential target for the intervention of renal fibrosis.

SUMMARY OF THE INVENTION

The object of the present invention is to provide a novel use of an urushiol compound, coded as GQ-5, isolated from *Resina Toxicodendri*.

The present invention provides a use of an urushiol compound GQ-5 in preparation of pharmaceutical compositions for inhibiting Smad3 phosphorylation.

In the present invention, inventors continue the research of the component of *Resina Toxicodendri* GQ-5, and demonstrate that treatment with GQ-5 significantly inhibited the progression of interstitial fibrosis in the unilateral ureteral obstruction (UUO) model. We further demonstrate that the anti-fibrotic effect of GQ-5 might be mediated by selective inhibition of TGF-β1-induced Smad3 phosphorylation.

In accordance with the present invention, the urushiol compound is isolated from *Resina Toxicodendri*.

In accordance with the present invention, the structural formula of the phenolic compound is:

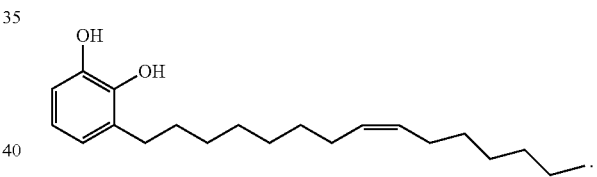

The results of experiments of the present invention verify that the urushiol compound GQ-5 inhibited the interaction of Smad3 with TβRI, inhibited subsequent phosphorylation of Smad3, reduced nuclear translocation of Smads complex, and suppressed the transcription of major fibrotic genes such as α-smooth muscle actin (α-SMA), collagen I and fibronectin. Therefore, GQ-5 could be a potent and selective inhibitor of TGF-β1-induced Smad3 phosphorylation, and be used to prepare pharmaceutical compositions for inhibiting Smad3 phosphorylation.

BRIEF DESCRIPTION OF THE DRAWINGS

For a fuller understanding of the nature and advantages of the invention, as well as a preferred mode of use, reference should be made to the following detailed description read in conjunction with the accompanying drawings, in which:

FIG. 3A illustrates Western blot analysis of p-Smad3 and p-Smad2 in NRK 52E cells.

FIG. 3B illustrates Western blot analysis of p-Smad3 and p-Smad2 in NRK 49F cells. Data were expressed as mean±SD of three independent experiments. ANOVA, p<0.05 in p-Smad3 expression in GQ-5 treated cells.

FIG. 5A illustrates Western blot analysis of Smad4 and Smad7.

FIG. 5B illustrates Western blot analysis of p-p38, p38, p-PI3K, PI3K, p-ERK, and ERK. Data were expressed as mean±SD of three independent experiments.

FIG. 6A illustrates immunohistochemical staining for p-Smad3 and p-Smad2.

FIG. 6B illustrates Western blots analysis of p-Smad3 and p-Smad2 in UUO rats. Data were shown as mean±SD of 6 rats. *p<0.05 vs UUO+vehicle group.

FIG. 7A illustrates Western blot analysis of Smad4 and Smad7 in UUO rats.

FIG. 7B illustrates Western blot analysis of p-p38, p38, p-PI3K, PI3K, p-ERK, and ERK in UUO rats. Data were shown as mean±SD of 6 rats.

FIG. 10A illustrates real-time PCR of α-SMA, collagen I and fibronectin in NRK 52E cells.

FIG. 10B illustrates real-time PCR of α-SMA, collagen I and fibronectin in NRK 49F cells. Data were expressed as mean±SD of three independent experiments. ANOVA, p<0.05 in GQ-5 treated cells in A&B; *p<0.05 vs untreated cells.

FIG. 11A illustrates Western blot was performed to examine the protein expression of α-SMA, collagen I and fibronectin in NRK 52E cells.

FIG. 11B illustrates Western blot was performed to examine the protein expression of α-SMA, collagen I and fibronectin in NRK 49F cells. Data were expressed as mean±SD of three independent experiments. ANOVA, p<0.05 in GQ-5 treated cells in A&B; *p<0.05 vs untreated cells.

FIG. 12A illustrates HE and mason staining of UUO kidneys.

FIG. 12B illustrates real-time PCR analysis of α-SMA, collagen I and fibronectin of UUO kidneys.

FIG. 12C illustrates immunohistochemical staining for α-SMA, collagen I and fibronectin of UUO kidneys.

FIG. 12D illustrates Western blot analysis of α-SMA, collagen I and fibronectin of UUO kidneys. Data were shown as mean±SD of 6 rats. * p<0.05 vs sham groups; # p<0.05 vs UUO+vehicle groups.

FIG. 13A illustrates that cell lysates were immunoprecipitated with α-TβRI, followed by immunoblotting using antibodies against Smad3, Smad2, TβRII and TβRI.

FIG. 13B illustrates that cell lysates were immunoprecipitated with a-Smad3, followed by immunoblotting using antibodies against Smad3, TβRII and TβRI.

FIG. 13C illustrates that cell lysates were immunoprecipitated with a-Smad2, followed by immunoblotting using antibodies against Smad2, TβRII and TβRI. Data were expressed as mean±SD of three independent experiments. *p<0.05 vs GQ-5 untreated cells under TGF-β1 stimulation.

FIG. 14A illustrates that kidney homogenates were immunoprecipitated with anti-TβRI, followed by immunoblotting using antibodies against Smad3, Smad2, TβRII and TβRI.

FIG. 14B illustrates that kidney homogenates were immunoprecipitated with α-Smad3, followed by immunoblotting using antibodies against Smad3, TβRII and TβRI.

FIG. 14C illustrates that kidney homogenates were immunoprecipitated with α-Smad2, followed by immunoblotting using antibodies against Smad2, TβRII and TβRI. Data were expressed as mean±SD of three independent experiments *p<0.05 vs vehicle treated UUO.

DETAILED DESCRIPTION OF THE INVENTION

Figures 1, 2:
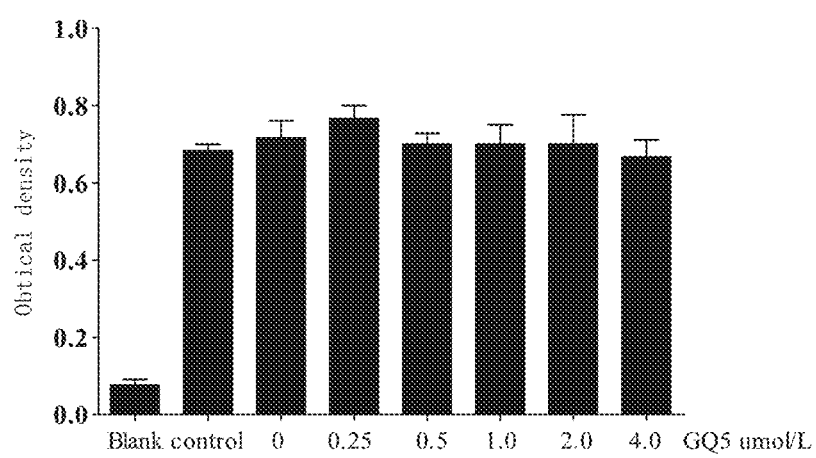
FIG. 1 illustrates the NMR data of GQ-5.
FIG. 2 illustrates the MTT tests of GQ-5 in NRK 52E cells.

A further illustration of the invention may be described with reference to the following examples.

Example 1

Preparation of the Urushiol Compound GQ-5

To isolate GQ-5, the dried resins of *Toxicodendron vernicifluum* (17 kg) (Yunnan Corporation of MateriaMedica, Kunming, P. R. China) were extracted with 80% ethanol (3×20 L) at room temperature. The extracts were concentrated under reduced pressure, and suspended in water followed by partition with ethyl acetate (3×5 L). The extract (220 g) from ethyl acetate was submitted to a silica gel column (200-300 mesh, 12×150 cm, 2.5 kg, Qingdao Marine Chemical Inc., Qingdao, P.R. China), eluted with a gradient of $CHCl_3MeOH$ (100:0-80:20) to yield 10 fractions. The fraction 4 (15 g) was subjected to a MCI gel CHP 20P column (75-150 μm, Mitsubishi Chemical Industries, Tokyo, Japan), eluted with gradient aqueous acetone (80:20-100:0) to yield fractions 4.1 and 4.2. Among them, the fraction 4.2 (11.3 g) was filtrated on Sephadex LH-20 ($CHCl_3MeOH$, 6:4, Amersham Pharmacia, Uppsala, Sweden) to yield GQ-5 (10 g).

Example 2

Identification of the Urushiol Compound GQ-5

The spectroscopic and chemical methods were used to identify the structure of GQ-5. The $^1H$ NMR spectrum using Bruker DRX-500 NMR spectrometer (Bruker Daltonics, Germany) indicated the diagnostic signals of one 1,2,4-trisubstituted benzene group, one methyl, and one aliphatic chain. The $^{13}$C NMR and DEPT spectra revealed one methyl, five methine, and three quaternary carbons (two of them are oxygenated). Mass spectra (ESI-MS) (API QSTAR Pulsar 1 spectrometer, AB SCIEX, USA) and high resolution ELMS (AutospecPrimier P776 instrument, Waters, USA) analyses indicated that the molecular formula of GQ-5 was $C_{21}H_{34}O_2$. The NMR data of GQ-5 were in agreement with those of 3-[(Z)-pentadec-8-enyl]catechol. In addition, the position and geometry of the double bond in the side chain was confirmed by total chemical synthesis.

Example 3

The Purity Determination of the Urushiol Compound GQ-5

The purity of GQ-5 was determined by analytic HPLC using RP-18 column under 280, 254, 230, 225 and 210 nm, and then eluted by gradient aqueous MeOH (85%400%, 0-20 min) Only one symmetric peak was found in all the chromatograms in different detection conditions, indicating that GQ-5 is a HPLC grade pure compound (FIG. 1). Consistently, there was no impurity present in the $^1$H NMR spectrum.

Example 4

Toxicological Experiment of the Urushiol Compound GQ-5 in Mice

To test the toxicity of GQ-5, 20 C57BL/6J little male mice which are 7-8 months old, healthy and clean, their weights are between 20 and 22 gram. Antisepsis the feed and water, before and in the layoff period of the test, all the mice should be feed under the normal feeding condition.

Dissolve GQ-5 in 0.5% propylene glycol, this liquor is given to little mice by intraperitoneal injection. The dosage of GQ-5 was 10, 40, 200, and 800 mg/kg body weight of mice. After administration, they are observed for 7 days. Mice intra-peritoneal injected with single dose of GQ-5 up to 800 mg/kg did not die or developed any adverse event during 7-day observation.

Example 5

Toxicological Experiment of the Urushiol Compound GQ-5

To test the toxicity of GQ-5, rat proximal tubular cells (NRK52E) were seeded into 96-well plates in a volume of 200 μl per well ($1\times10^5$ cell/ml) and incubated for 24 hours to allow cells to attach. The cells were then incubated with indicated amount of GQ-5 for 1 h. Cell viability was determined by addition of 20 μl of 3-(4,5-dimethylthiazol-2-yl)-2,5-diphenyltetrazolium bromide (MTT) at a concentration of 5 mg/ml. After incubation for 4 hours, the medium was removed and 150 μl of DMSO was added to dissolve the formazan crystals. The absorbance was read at 540 nm by using iMark™Microplate Reader (Bio-Rad). As shown in FIG. 2, GQ-5, over a complete pharmacologically relevant dose (0.25-4 μM), did not affect the viability and proliferation of the cells.

Example 6

GQ-5 Dose-Dependently Inhibits TGF-β1-Induced Smad3 Phosphorylation In Vitro

1. Cells.

NRK52E and NRK49F cells were cultured in DMEM-Ham's medium supplemented with 10% fetal bovine serum. The cells reached at approximately 50% confluence were used for in vitro experiments. Cells were serum-starved for 12 h, and randomized into 6 groups: (1) Controls; (2) GQ-5 only; (3) TGF-β1 only; (4) TGF-β1+GQ-5 0.1 μM; (5) TGF-β1+GQ-5 0.5 μM; (6) TGF-β1+GQ-5 2.5 μM.

2. Sample Source and Preparation (1) Controls: incubated with DMEM for 2 h;

(2) GQ-5 only: pre-treated with GQ-5 (2.5 μM) for 1 h, followed with DMEM for 1 h (3) TGF-β1 only: pre-treated with DMSO (0.1%) for 1 h, followed with TGF-β1 (10 ng/ml) for 1 h (4) TGF-β1+GQ-5 0.1 μM: pre-treated with GQ-5 (0.1 μM) for 1 h, followed with TGF-β1 (10 ng/ml) for 1 h (5) TGF-β1+GQ-5 0.5 μM: pre-treated with GQ-5 (0.5 μM) for 1 h, followed with TGF-β1 (10 ng/ml) for 1 h (6) TGF-β1+GQ-5 2.5 μM: pre-treated with GQ-5 (2.5 μM) for 1 h, followed with TGF-β1 (10 ng/ml) for 1 h.

3. Experimental Methods

GQ-5 was dissolved in DMSO. Cells were treated as described. Cell lysates were immunoblotted with antibodies against phospho-Smad3, Smad3, phospho-Smad2, Smad2.

4. Results

Figure 3A:
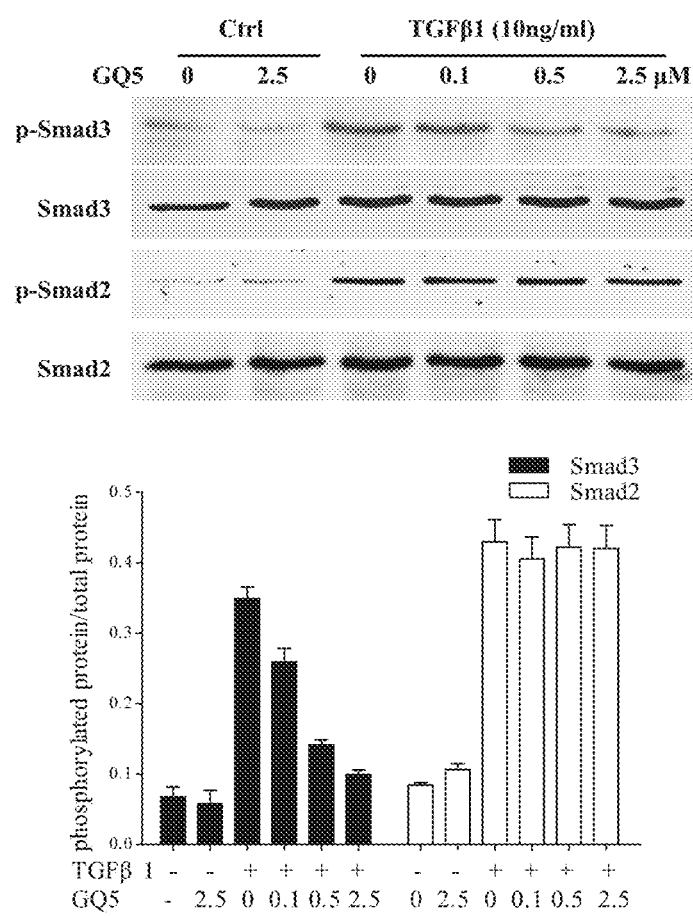
FIGS. 3A-3B illustrate GQ-5 dose-dependently inhibits TGF-β1-induced Smad3 phosphorylation in vitro.
Figure 3B:
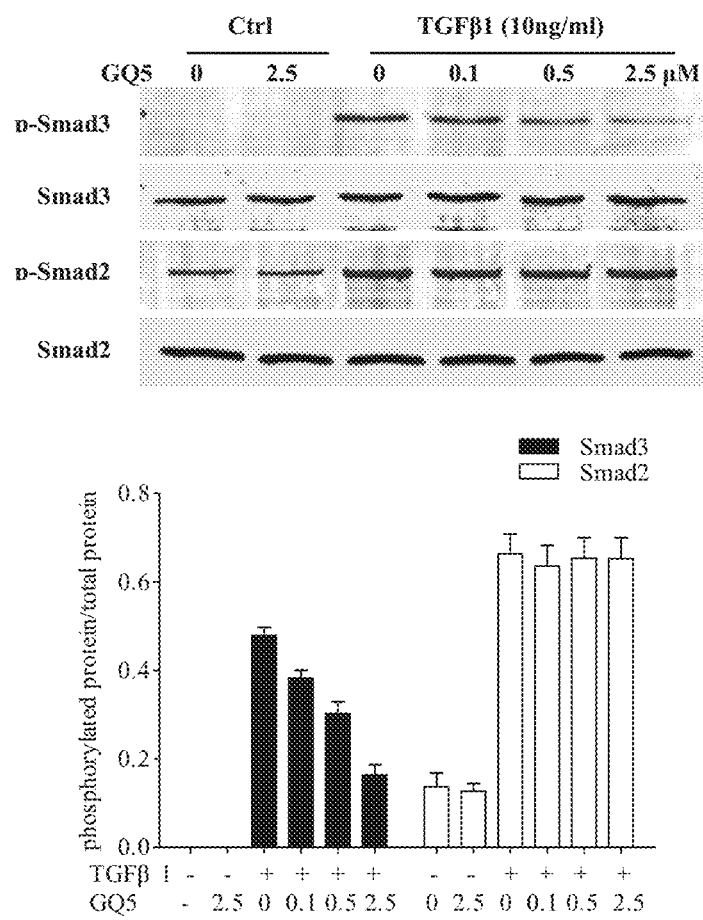
Figure 5A:
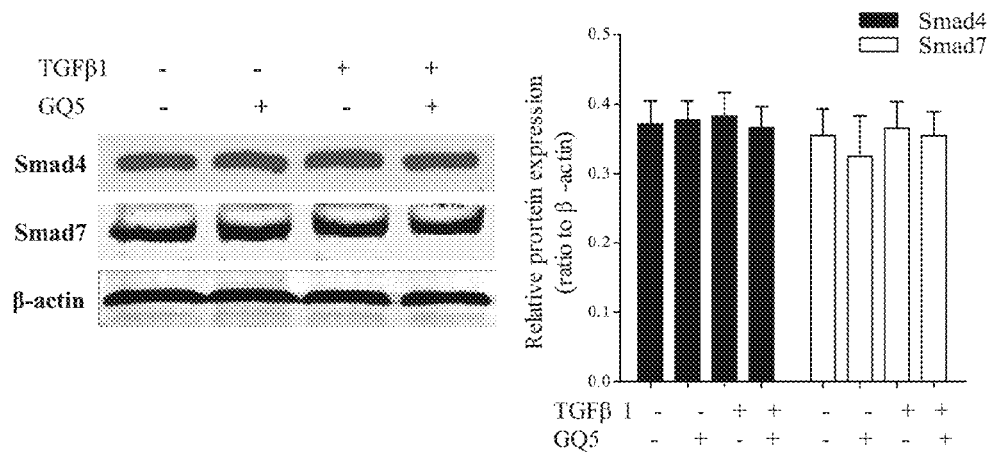
FIG. 5A-5B illustrate GQ-5 does not affect TGF-β1-induced Smad4, Smad7 expression or p38, PI3K, ERK phosphorylation in vitro.
Figure 5B:
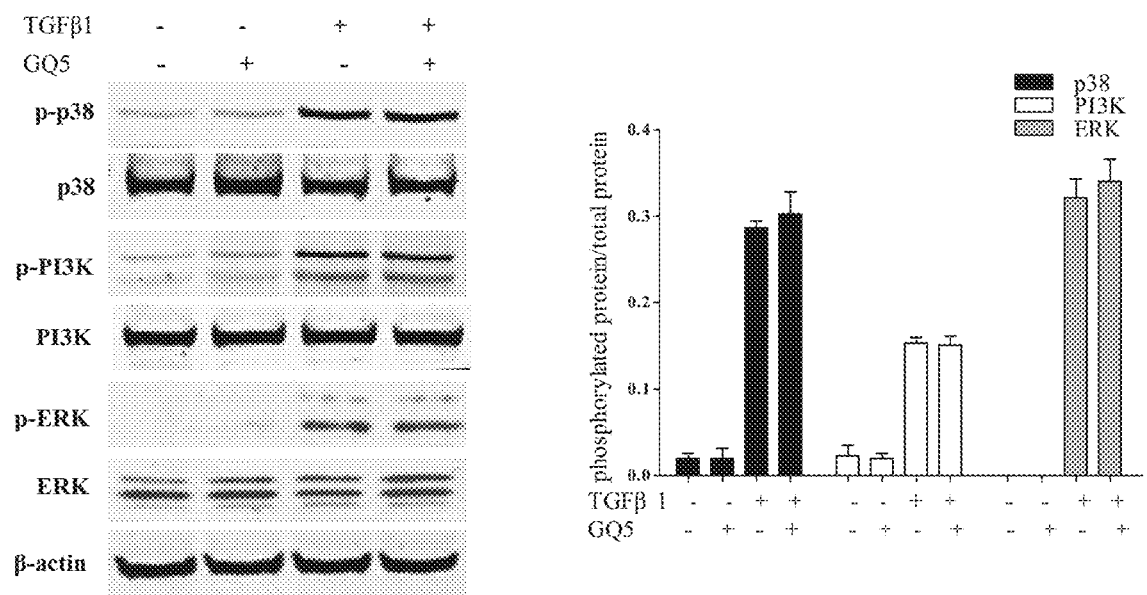

As shown in FIGS. 5A-5B, incubation with TGF-β1 significantly induced phosphorylation of Smad2 and Smad3 in both NRK52E (FIG. 3A) and NRK49F cells (FIG. 3B). GQ-5 treatment attenuated TGF-β1-induced Smad3 phosphorylation in a dose-dependent manner, but did not affect TGF-β1-induced Smad2 phosphorylation. The inhibitory effect of GQ-5 was almost undetectable in NRK52E and NRK49F cells in the absence of TGF-β1 stimulation.

Example 7

GQ-5 Time-Dependently Inhibits TGF-β1-Induced Smad3 Phosphorylation In Vitro

1. Cells.

NRK52E cells were cultured in DMEM-Ham's medium supplemented with 10% fetal bovine serum. The cells reached at approximately 50% confluence were used for in vitro experiments. Cells were serum-starved for 12 h, and randomized into 8 groups: (1) Controls; (2) GQ-5 only; (3) TGF-β1 0.5 h; (4) TGF-β1 0.5 h+GQ-5; (5) TGF-β1 1.0 h; (6) TGF-β1 1.0 h+GQ-5; (7) TGF-β1 3.0 h; (8) TGF-β1 3.0 h+GQ-5;

2. Sample Source and Preparation (1) Controls: incubated with DMEM for 2 h;

(2) GQ-5 only: pre-treated with GQ-5 (2.5 μM) for 1 h, followed with DMEM for 1 h (3) TGF-β1 0.5 h: pre-treated with DMSO (0.1%) for 1 h, followed with TGF-β1 (10 ng/ml) for 0.5 h (4) TGF-β1 0.5 h+GQ-5: pre-treated with GQ-5 (2.5 μM) for 1 h, followed with TGF-β1 (10 ng/ml) for 0.5 h (5) TGF-β1 1.0 h: pre-treated with DMSO (0.1%) for 1 h, followed with TGF-β1 (10 ng/ml) for 1.0 h (6) TGF-β1 1.0 h+GQ-5: pre-treated with GQ-5 (2.5 μM) for 1 h, followed with TGF-β1 (10 ng/ml) for 1.0 h (7) TGF-β1 3.0 h: pre-treated with DMSO (0.1%) for 1 h, followed with TGF-β1 (10 ng/ml) for 3.0 h (8) TGF-β1 3.0 h+GQ-5: pre-treated with GQ-5 (2.5 μM) for 1 h, followed with TGF-β1 (10 ng/ml) for 3.0 h 3. Experimental Methods GQ-5 was dissolved in DMSO. Cells were treated as described. Cell lysates were immunoblotted with antibodies against phospho-Smad3, Smad3, phospho-Smad2, and Smad2.

4. Results

Figure 4:
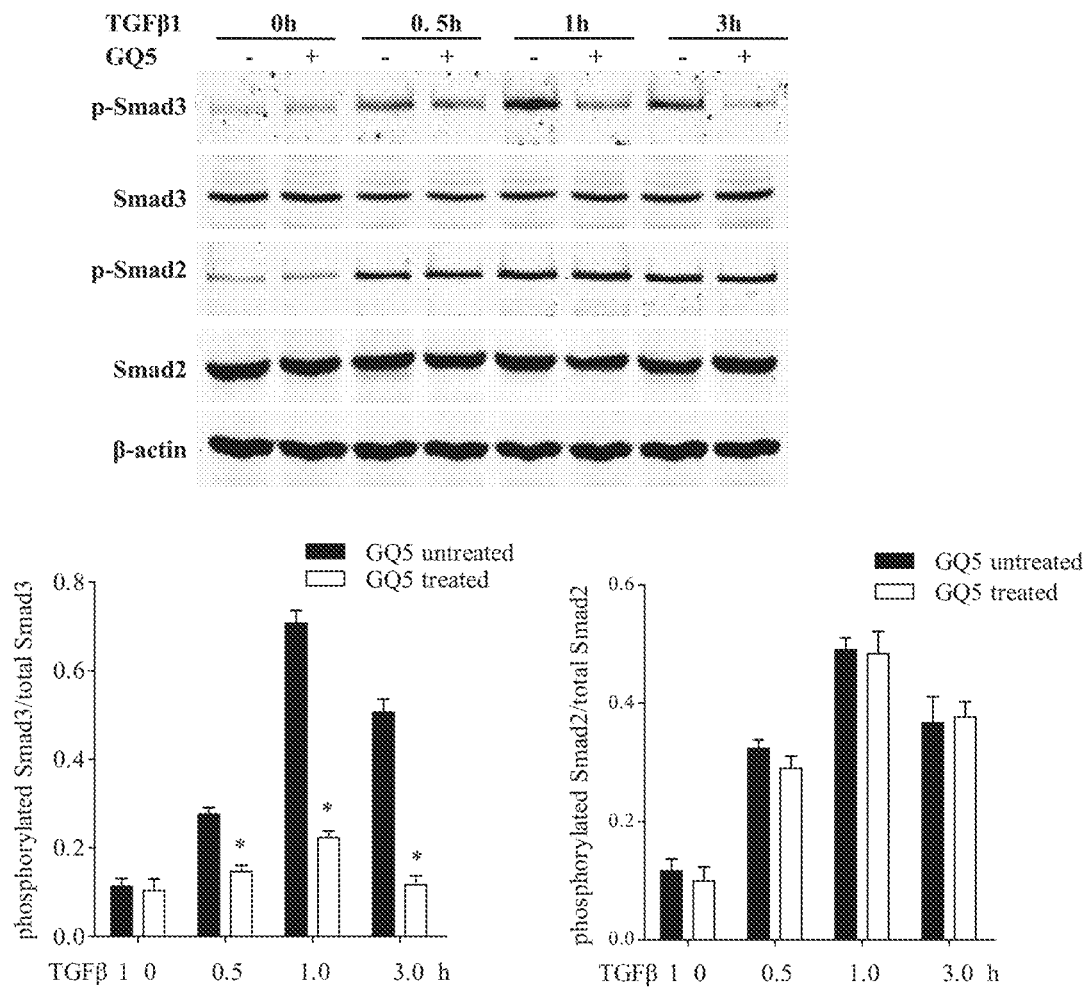
FIG. 4 illustrates GQ-5 time-dependently inhibits TGF-β1-induced Smad3 phosphorylation in vitro. Cell lysates were immunoblotted with antibodies against p-Smad3, p-Smad2, total Smad3 and total Smad2. Data were expressed as mean±SD of three independent experiments. * p<0.05, vs GQ-5 untreated cells with TGF-β1 stimulation.

As shown in FIG. 4, incubation with TGF-β1 significantly induced phosphorylation of Smad2 and Smad3 in NRK52E cells. GQ-5 treatment attenuated TGF-β1-induced Smad3 phosphorylation in a time-dependent manner, but did not affect TGF-β1-induced Smad2 phosphorylation.

Example 8

GQ-5 does not Inhibit TGF-β1-Induced Smad4 or Smad7 Expression, Nor p38, PI3K, ERK Phosphorylation In Vitro 1. Cells.

NRK52E and NRK49F cells were cultured in DMEM-Ham's medium (Gibco, Life Techologies, NY, USA) supplemented with 10% fetal bovine serum (Gibco, Life Techologies, NY, USA). The cells reached at approximately 50% confluence were used for in vitro experiments. Cells were serum-starved for 12 h, and randomized into 4 groups: (1) Controls; (2) GQ-5 only; (3) TGF-β1 only; (4) TGF-β1+GQ-5

2. Sample Source and Preparation (1) Controls: incubated with DMEM for 2 h;

(2) GQ-5 only: pre-treated with GQ-5 (2.5 μM) for 1 h, followed with DMEM for 1 h (3) TGF-β1 only: pre-treated with DMSO (0.1%) for 1 h, followed with TGF-β1 (10 ng/ml) for 1 h (4) TGF-β1+GQ-5: pre-treated with GQ-5 (2.5 nM) for 1 h, followed with TGF-β1 (10 ng/ml) for 1 h 3. Experimental Methods GQ-5 was dissolved in DMSO. Cells were treated as described. cell lysates were immunoblotted with antibodies against Smad4, Smad7, phospho-p38, p38, phospho-PI3K, PI3K, phosphor-ERK, and ERK.

4. Results

As shown in FIGS. 5A-5B, GQ-5 did not affect the protein expression of Smad4 or Smad7, nor the TGF-β1-induced phosphorylation of p38, ERK and PI3K.

Example 9

GQ-5 Selectively Inhibits the Phosphorylation of Smad3 and Smad2 In Vivo

1. Animal Model

Male Sprague-Dawley rats with body weight 200 to 250 g were randomized into 4 groups (n=6 in each group): (1) sham operated rats; (2) UUO rats; (3) UUO+GQ-5 d1 rats; (4) UUO+GQ-5 d7 rats.

2. Sample Source and Preparation

GQ-5 was dissolved in 5% propylene glycol.

(1) Sham operated rats: daily intraperitoneal injection of 5% propylene glycol;

(2) UUO rats: daily intraperitoneal injection of 5% propylene glycol;

(3) UUO+GQ-5 d1 rats: daily intraperitoneal injection of GQ-5 (40 mg/kg body weight) right after UUO;

(4) UUO+GQ-5 d7 rats: daily intraperitoneal injection of GQ-5 (40 mg/kg body weight) 7 days after UUO.

3. Experimental Methods

UUO was performed using an established protocol as described. GQ-5 was dissolved in 5% propylene glycol. Rats were administrated with GQ-5 as described before. All the rats were sacrificed 14 days after UUO. Immunohistochemical staining and Western blot analyses were performed to examine the Smad3 and Smad2 phosphorylation in kidney tissue.

4. Results

Figure 6A:
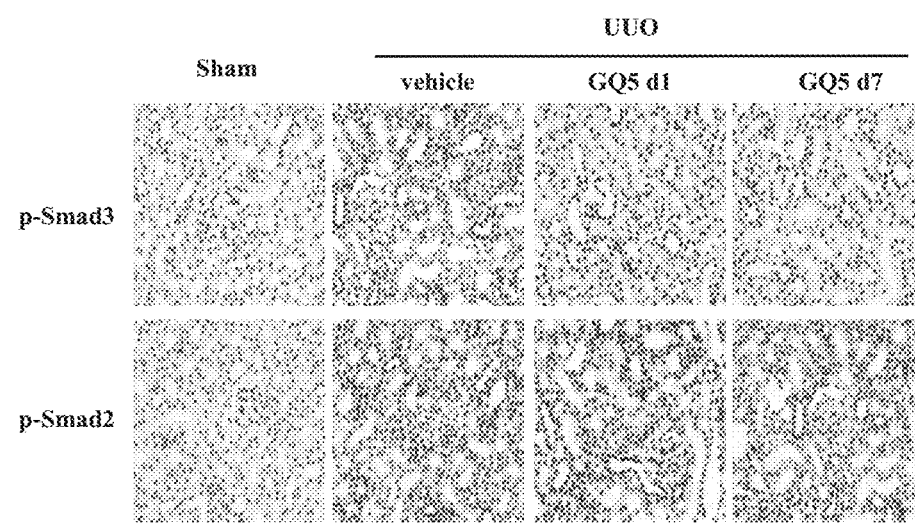
FIG. 6A-6B illustrate GQ-5 selectively inhibits Smad3 phosphorylation in UUO rats.
Figure 6B:
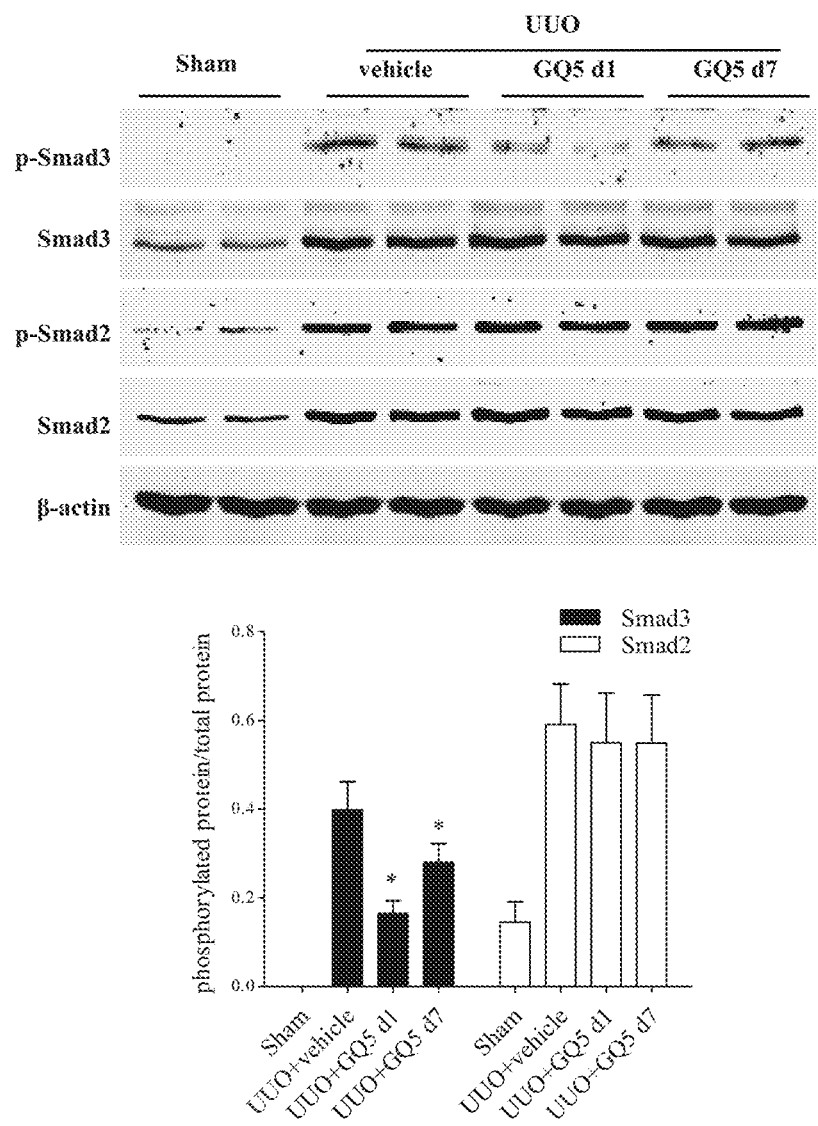

As shown in FIG. 6, the phosphorylation of both Smad3 and Smad2 in renal tissue was significantly increased in UUO rats compared to sham controls. Treatment of GQ-5 significantly inhibited Smad3 but not Smad2 phosphorylation.

Example 10

GQ-5 does not Affect Smad4, Smad7 Expression or p38, PI3K, ERK Phosphorylation in UUO Kidneys 1. Animal Model Male Sprague-Dawley rats with body weight 200 to 250 g were randomized into 3 groups (n=6 in each group): (1) sham operated rats; (2) UUO rats; (3) UUO+GQ-5 rats.

2. Sample Source and Preparation

GQ-5 was dissolved in 5% propylene glycol.

(1) Sham operated rats: daily intraperitoneal injection of 5% propylene glycol;

(2) UUO rats: daily intraperitoneal injection of 5% propylene glycol;

(3) UUO+GQ-5 rats: daily intraperitoneal injection of GQ-5 (40 mg/kg body weight) right after UUO;

3. Experimental Methods

UUO was performed using an established protocol as described. GQ-5 was dissolved in 5% propylene glycol. Rats were administrated with GQ-5 as described before. All the rats were sacrificed 14 days after UUO. Western blot analyses were performed to examine the Smad4, Smad7 expression and p38, PI3K, ERK phosphorylation.

4. Results

Figure 7A:
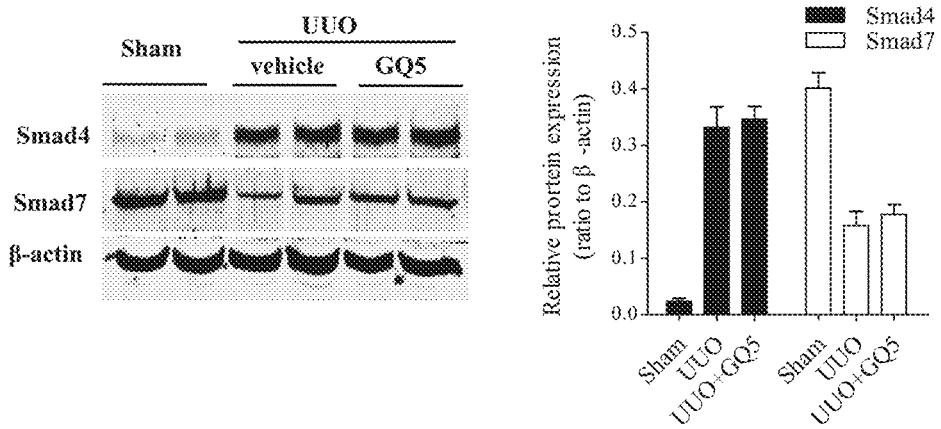
FIG. 7A-7B illustrate GQ-5 does not affect Smad4, Smad7 expression or p38, PI3K, ERK phosphorylation in UUO rats.
Figure 7B:
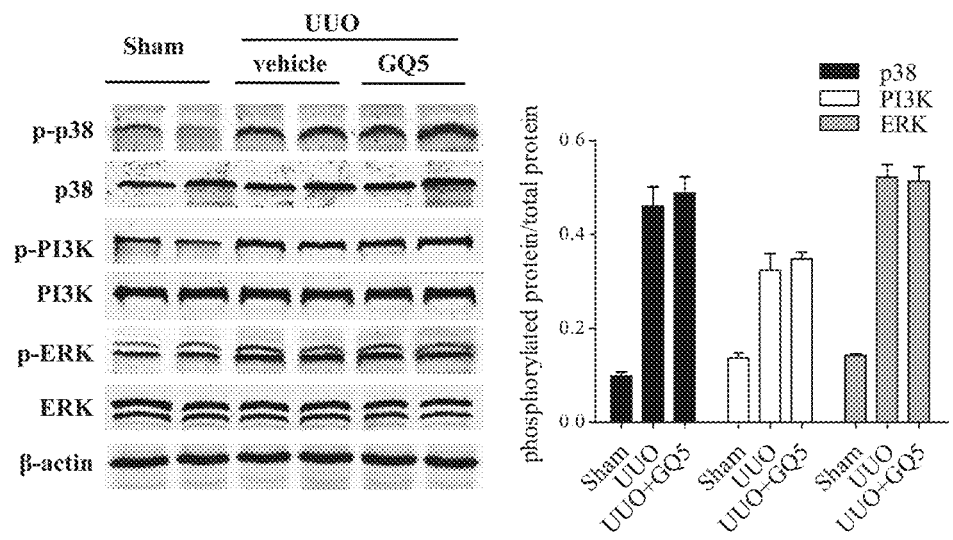

As shown in FIGS. 7A-7B, GQ-5 did not affect the expression of Smad4 and Smad7, or the phosphorylation of p38, PI3K or ERK in UUO rats.

Example 11

GQ-5 Reduced the TGF-β1-Induced Smad3 Nuclear Translocation

1. Cells.

NRK52E cells were cultured in DMEM-Ham's medium supplemented with 10% fetal bovine serum. The cells reached at approximately 50% confluence were used for in vitro experiments. Cells were serum-starved for 12 h, and randomized into 3 groups: (1) Controls; (2) TGF-β1 only; (3) TGF-β1+GQ-5.

2. Sample Source and Preparation (1) Controls: incubated with DMEM for 2 h;

(2) TGF-β1 only: pre-treated with DMSO for 1 h, followed with TGF-β1 (10 ng/ml) for 2 h (3) TGF-β1+GQ-5: pre-treated with GQ-5 (2.5 μM) for 1 h, followed with TGF-β1 (10 ng/ml) for 2 h 3. Experimental Methods GQ-5 was dissolved in DMSO. Cells were treated as described Immunofluorescence staining was performed to examine the nuclear translocation of Smad2, Smad3, and Smad4.

4. Results

Figure 8:
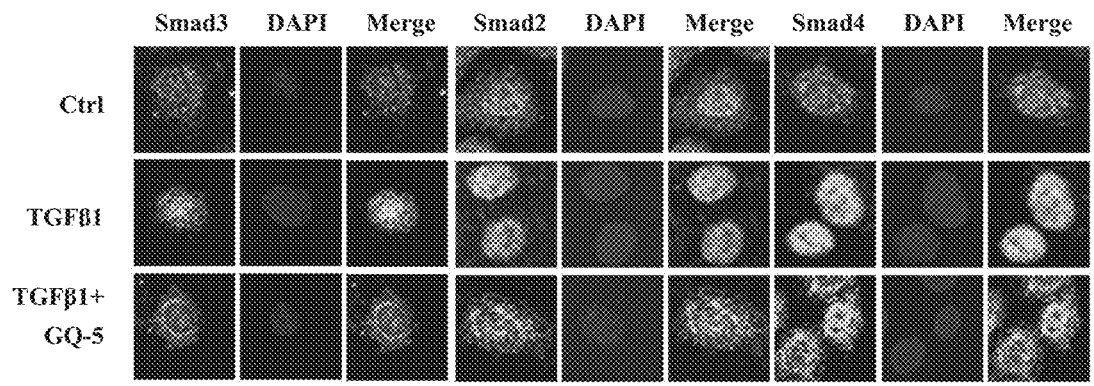
FIG. 8 illustrates GQ-5 reduces the TGF-β1-induced Smad3 nuclear translocation Immunofluorescence staining revealed that GQ-5 treatment inhibited TGFβ1-induced nuclei translocation of Smad3, Smad2, and Smad4 (800×).

As shown in FIG. 8, immunofluorescence staining reveled that pre-incubating NRK52E cells with GQ-5 significantly reduced the TGF-β1-induced Smad3 nuclear translocation. Treatment with GQ-5 also reduced nuclear translocation of Smad2 and Smad4.

Example 12

GQ-5 Reduced the TGF-β1-Induced Smad3-Dependent Collagen I Promoter Activity

1. Cells.

NRK52E cells were cultured in DMEM-Ham's medium supplemented with 10% fetal bovine serum. The cells reached at approximately 50% confluence were used for in vitro experiments. Cells were transiently transfected with a Smad3 responsive promoter p(GAGA)12-luc plasmid. PGL3 basic plasmid was co-transfected into the cells as control. Cells were serum-starved for 12 h, and randomized into 6 groups: (1) Controls; (2) GQ-5 only; (3) TGF-β1 only; (4) TGF-β1+GQ-5 0.1 μM; (5) TGF-β1+GQ-5 0.5 μM; (6) TGF-β1+GQ-5 2.5 μM 2. Sample Source and Preparation (1) Controls: transfected with PGL3 basic plasmid and incubated with DMEM for 24 h;

(2) GQ-5 only: transfected with p(GAGA)12-luc plasmid, pre-treated with GQ-5 (2.5 μM) for 1 h, followed with DMEM for 24 h (3) TGF-β1 only: transfected with p(GAGA)12-luc plasmid, pre-treated with DMSO for 1 h, followed with TGF-β1 (10 ng/ml) for 24 h (4) TGF-β1+GQ-5 0.1 μM: transfected with p(GAGA)12-luc plasmid, pre-treated with GQ-5 (0.1 mM) for 1 h, followed with TGF-β1 (10 ng/ml) for 24 h (5) TGF-β1+GQ-5 0.5 μM: transfected with p(GAGA)12-luc plasmid, pre-treated with GQ-5 (0.5 mM) for 1 h, followed with TGF-β1 (10 ng/ml) for 24 h (6) TGF-β1+GQ-5 2.5 μM: transfected with p(GAGA)12-luc plasmid, pre-treated with GQ-5 (2.5 mM) for 1 h, followed with TGF-β1 (10 ng/ml) for 24 h 3. Experimental Methods GQ-5 was dissolved in DMSO. Cells were treated as described. Promoter assays using a luciferase reporter system were performed to examine the Smad3-dependent collagen I promoter activity.

4. Results

Figure 9:
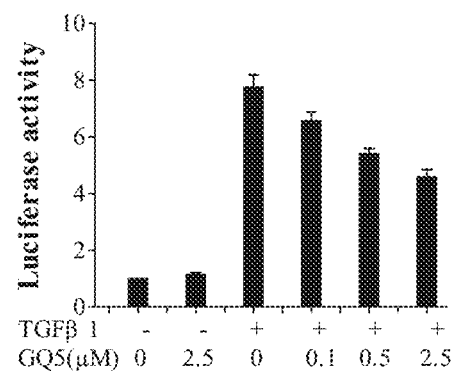
FIG. 9 illustrates GQ-5 reduces the TGF-β1-induced Smad3-dependent collagen I promoter activity. NRK 52E cells were co-transfected with p(CACA)-luc plasmid and PGL3, followed by TGF-β1 (10 ng/ml) stimulation for 24 h in the absence or presence of indicated doses of GQ-5. Relative luciferase activity was presented. Data were expressed as mean±SD of three independent experiments. ANOVA, p<0.05 in GQ-5 treated cells.

As shown in FIG. 9, treatment with GQ-5 significantly inhibited TGF-β1-induced Smad3-dependent collagen I promoter activity in a dose-dependent manner.

Example 13

GQ-5 Reduced the TGF-β1-Induced α-SMA, Collagen I and Fibronectin mRNA Expression 1. Cells.

NRK52E and NRK49F cells were cultured in DMEM-Ham's medium supplemented with 10% fetal bovine serum. The cells reached at approximately 50% confluence were used for in vitro experiments. Cells were serum-starved for 12 h, and randomized into 6 groups: (1) Controls; (2) GQ-5 only; (3) TGF-β1 only; (4) TGF-β1+GQ-5 0.1 μM; (5) TGF-β1+GQ-5 0.5 μM; (6) TGF-β1+GQ-5 2.5 μM 2. Sample Source and Preparation (1) Controls: incubated with DMEM for 36 h;

(2) GQ-5 only: pre-treated with GQ-5 (2.5 μM) for 1 h, followed with DMEM for 36 h (3) TGF-β1 only: pre-treated with DMSO for 1 h, followed with TGF-β1 (10 ng/ml) for 36 h (4) TGF-β1+GQ-5 0.1 μM: pre-treated with GQ-5 (0.1 μM) for 1 h, followed with TGF-β1 (10 ng/ml) for 36 h (5) TGF-β1+GQ-5 0.5 μM: pre-treated with GQ-5 (0.5 μM) for 1 h, followed with TGF-β1 (10 ng/ml) for 36 h (6) TGF-β1+GQ-5 2.5 μM: pre-treated with GQ-5 (2.5 μM) for 1 h, followed with TGF-β1 (10 ng/ml) for 36 h 3. Experimental Methods GQ-5 was dissolved in DMSO. Cells were treated as described. Cells were collected for mRNA extraction. Real-rime PCR was performed to examine the mRNA expression of α-SMA, collagen I and fibronectin.

4. Results

Figure 10A:
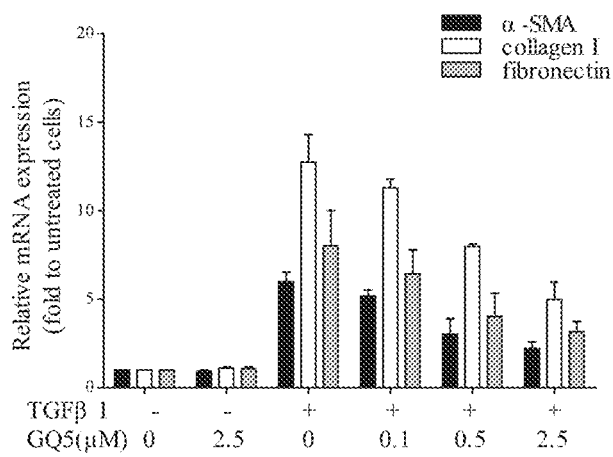
FIG. 10A-10B illustrate GQ-5 inhibits the TGF-β1-induced α-SMA, collagen I and fibronectin mRNA expression.
Figure 10B:
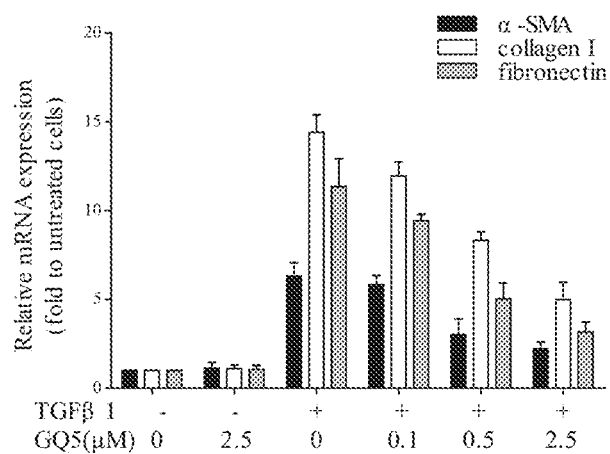
Figure 12A:
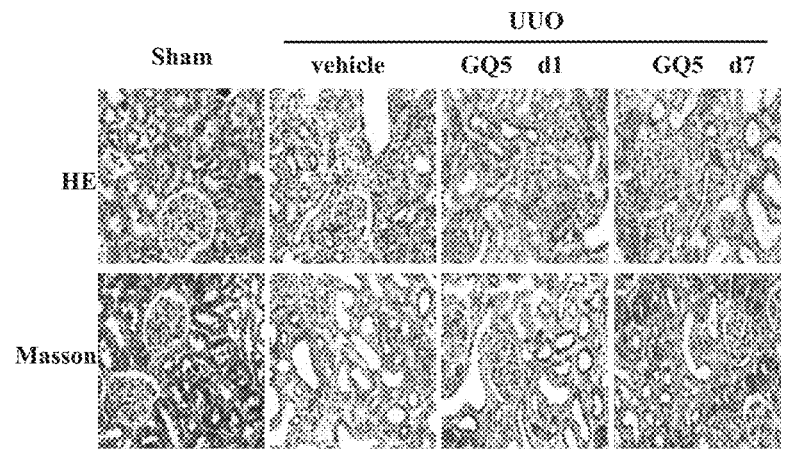
FIGS. 12A-12D illustrate GQ-5 ameliorates renal interstitial fibrosis initiating GQ-5 both right after (GQ-5 d1) and 7 days (GQ-5 d7) after operation.
Figure 12B:
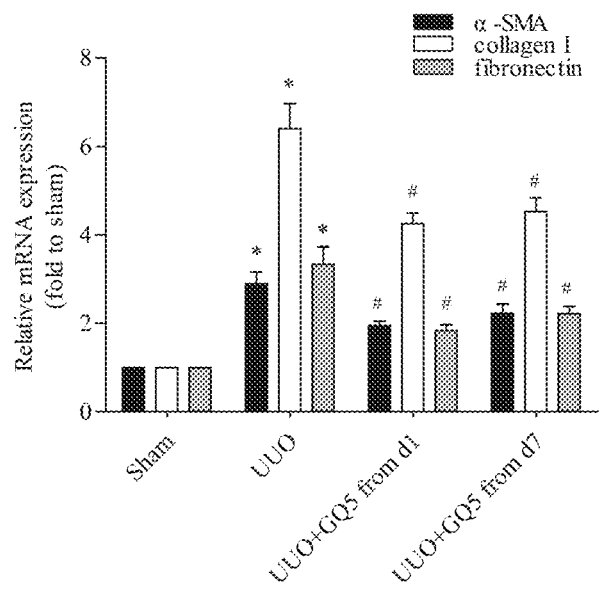
Figure 12C:
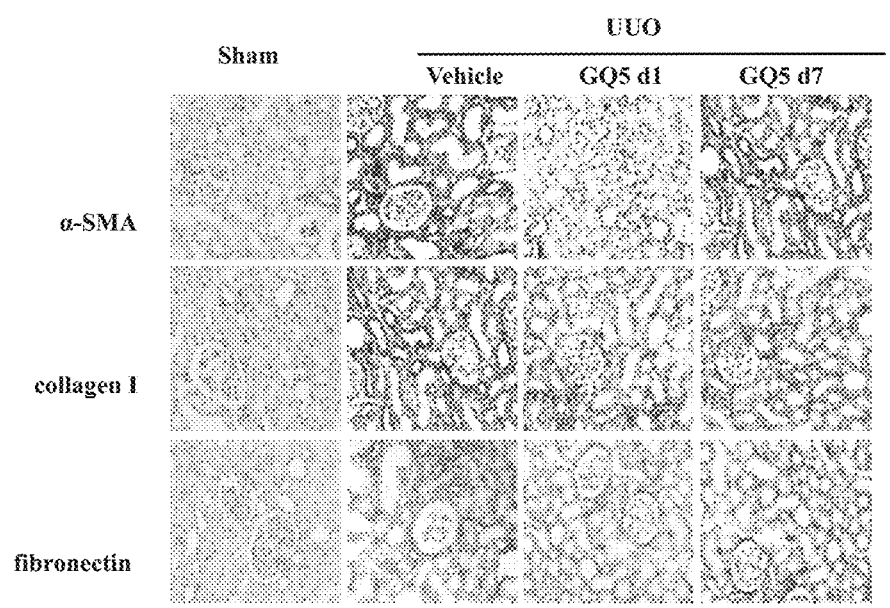
Figure 12D:
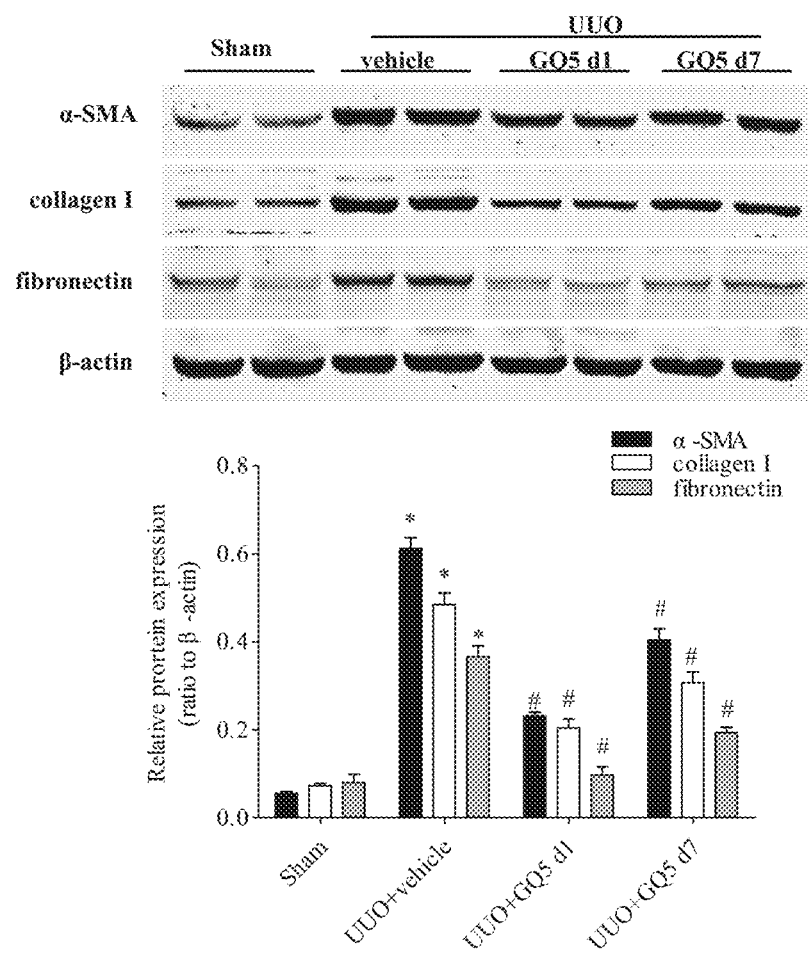

As shown in FIGS. 10A-10B, in compare with the control, treatment with GQ-5 significantly inhibited TGF-β1-induced mRNA expression of α-SMA, collagen I and fibronectin in NRK 52E (FIG. 12A) and NRK 49F cells (FIG. 12B).

Example 14

GQ-5 Reduced the TGF-β1-Induced α-SMA, Collagen I and Fibronectin Protein Expression 1. Cells.

NRK52E and NRK49F cells were cultured in DMEM-Ham's medium supplemented with 10% fetal bovine serum. The cells reached at approximately 50% confluence were used for in vitro experiments. Cells were serum-starved for 12 h, and randomized into 6 groups: (1) Controls; (2) GQ-5 only; (3) TGF-β1 only; (4) TGF-β1+GQ-5 0.1 μM; (5) TGF-β1+GQ-5 0.5 μM; (6) TGF-β1+GQ-5 2.5 μM 2. Sample Source and Preparation (1) Controls: incubated with DMEM for 48 h;

(2) GQ-5 only: pre-treated with GQ-5 (2.5 μM) for 1 h, followed with DMEM for 48 h (3) TGF-β1 only: pre-treated with DMSO for 1 h, followed with TGF-β1 (10 ng/ml) for 48 h (4) TGF-β1+GQ-5 0.1 μM: pre-treated with GQ-5 (0.1 μM) for 1 h, followed with TGF-β1 (10 ng/ml) for 48 h (5) TGF-β1+GQ-5 0.5 μM: pre-treated with GQ-5 (0.5 μM) for 1 h, followed with TGF-β1 (10 ng/ml) for 48 h (6) TGF-β1+GQ-5 2.5 μM: pre-treated with GQ-5 (2.5 μM) for 1 h, followed with TGF-β1 (10 ng/ml) for 48 h 3. Experimental Methods GQ-5 was dissolved in DMSO. Cells were treated as described. Cells lysates were immunebloted with antibodies against α-SMA, collagen I and fibronectin.

4. Results

Figure 11A:
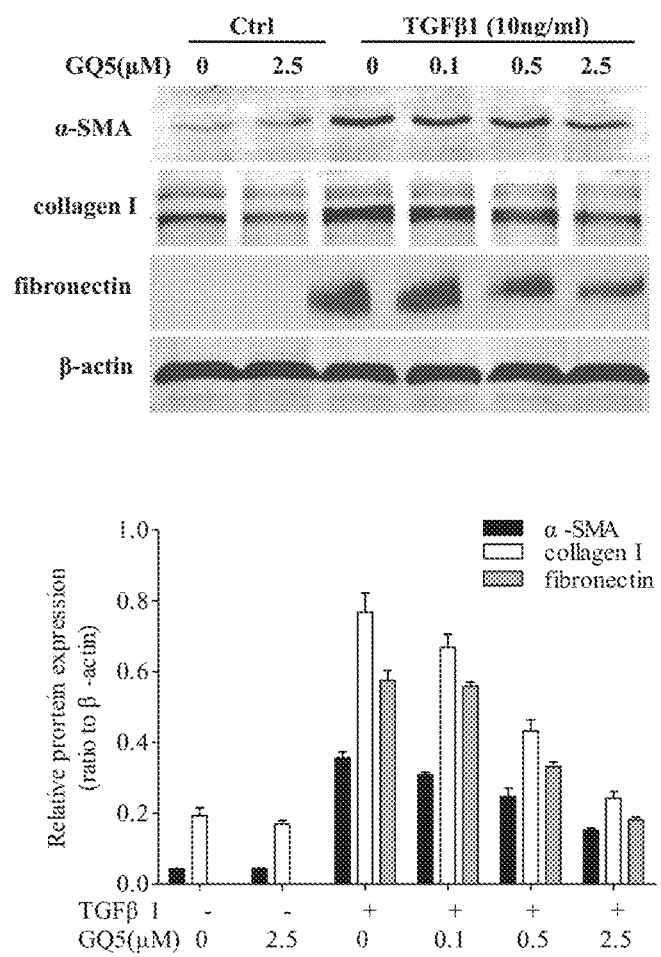
FIGS. 11A-11B illustrate GQ-5 inhibits the TGF-β1-induced α-SMA, collagen I and fibronectin protein expression.
Figure 11B:
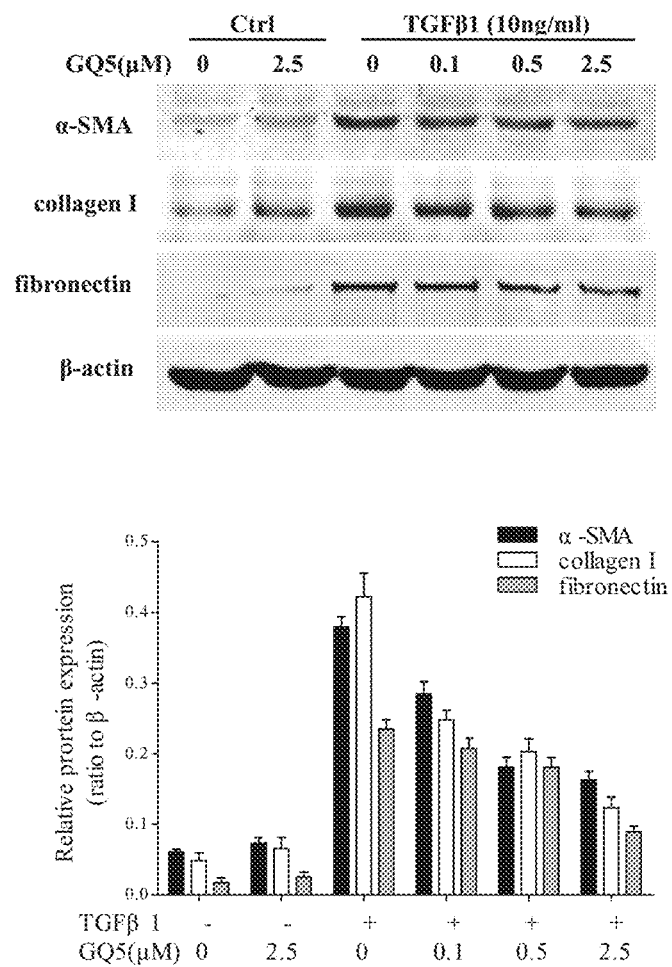
Figure 13A:
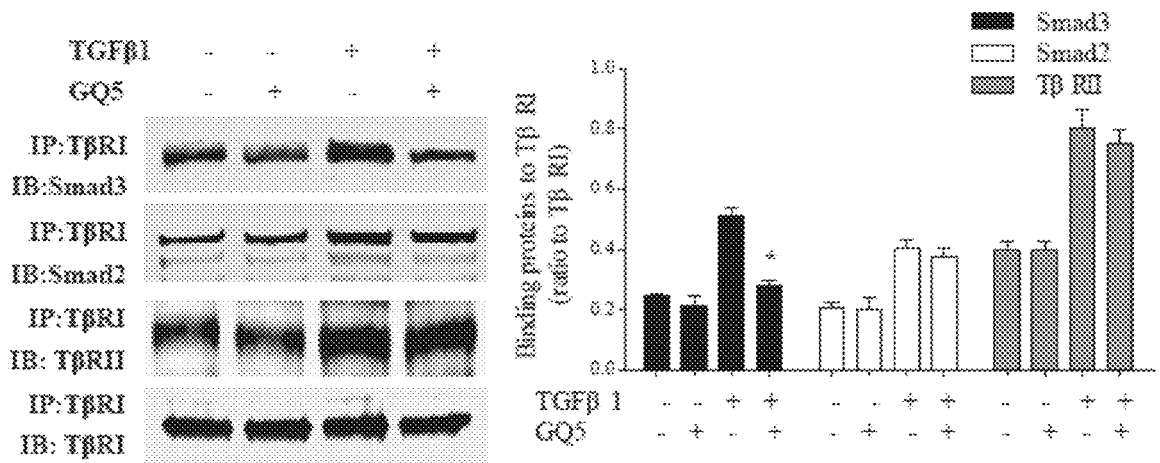
FIGS. 13A-13C illustrate GQ-5 selectively blocks the interaction of Smad3 with TβRI in vitro.
Figure 13B:
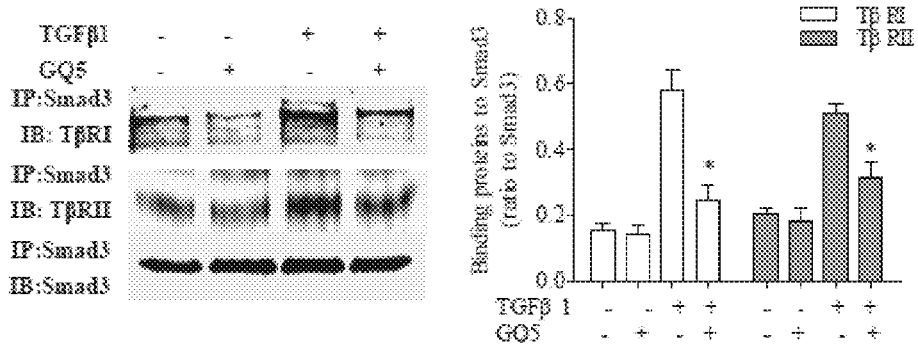

As shown in FIGS. 11A-11B, treatment with GQ-5 significantly inhibited TGF-β1-induced protein expression of α-SMA, collagen I and fibronectinin NRK 52E (FIG. 13A) and NRK 49F cells (FIG. 13B).

Example 15

GQ-5 Ameliorates Renal Interstitial Fibrosis after UUO

1. Animal Model

Male Sprague-Dawley rats were randomized into 4 groups (n=6 in each group): (1) sham operated rats; (2) UUO rats; (3) UUO+GQ-5 d1 rats; (4) UUO+GQ-5 d7 rats.

2. Sample Source and Preparation

GQ-5 was dissolved in 5% propylene glycol.

(1) Sham operated rats: daily intraperitoneal injection of 5% propylene glycol;

(2) UUO rats: daily intraperitoneal injection of 5% propylene glycol;

(3) UUO+GQ-5 d1 rats: daily intraperitoneal injection of GQ-5 (40 mg/kg body weight) right after UUO;

(4) UUO+GQ-5 d7 rats: daily intraperitoneal injection of GQ-5 (40 mg/kg body weight) 7 days after UUO.

3. Experimental Methods

UUO was performed using an established protocol as described. GQ-5 was dissolved in 5% propylene glycol. Rats were administrated with GQ-5 as described before. All the rats were sacrificed 14 days after UUO. HE staining, Masson trichrome staining were performed to examine the renal tissue injury, and Real-time PCR analyses, immunohistochemical staining, and Western blot analyses were performed to examine α-SMA, collagen I and fibronectin expression in kidney tissue 4. Results As shown in FIGS. 12A-12D, UUO rats exhibited marked interstitial inflammation and fibrosis in renal tissue stained with hematoxylin-eosin and Masson-trichrome. Treatment with GQ-5, either initiating right after or 7 days after operation, significantly reduced inflammatory cell infiltration and interstitial fibrosis score. Intervention with GQ-5 also significantly inhibited the up-regulation of α-SMA, collagen I and fibronectin in UUO rats at both mRNA and protein level, suggesting that treatment of GQ-5 not only prevented renal fibrosis, but also ameliorated established renal fibrosis.

Example 16

GQ-5 Selectively Blocks the Interaction of Smad3 with TβRI In Vitro

1. Cells.

NRK52E cells were cultured in DMEM-Ham's medium supplemented with 10% fetal bovine serum. The cells reached at approximately 50% confluence were used for in vitro experiments. Cells were serum-starved for 12 h, and randomized into 4 groups: (1) Controls; (2) GQ-5 only; (3) TGF-β1 only; (4) TGF-β1+GQ-5

2. Sample Source and Preparation (1) Controls: incubated with DMEM for 2 h;

(2) GQ-5 only: pre-treated with GQ-5 (2.5 nM) for 1 h, followed with DMEM for 1 h (3) TGF-β1 only: pre-treated with DMSO for 1 h, followed with TGF-β1 (10 ng/ml) for 1 h (4) TGF-β1+GQ-5: pre-treated with GQ-5 (2.5 nM) for 1 h, followed with TGF-β1 (10 ng/ml) for 1 h 3. Experimental Methods GQ-5 was dissolved in DMSO. Cells were treated as described. Cell lysates were collected for immunoprecipitation to examine the interaction among TGFβ type I receptor (TβRI), TβRII, Smad3 and Smad2.

4. Results

Figure 13C:
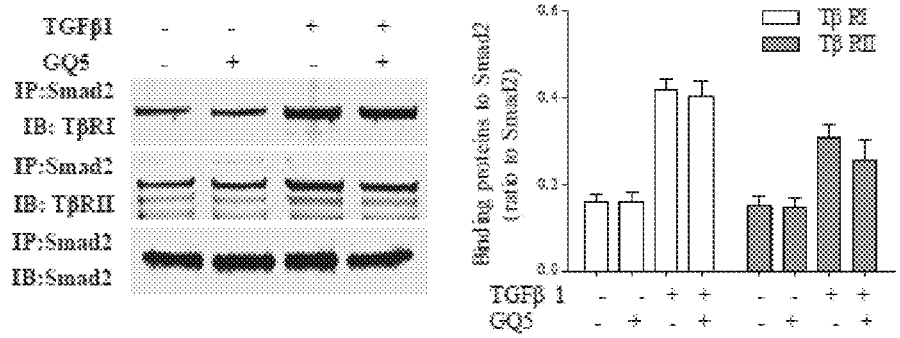

As shown in FIGS. 13A-13C, TβRI bound with TβRII, Smad2 and Smad3 upon TGF-β1 stimulation. Treatment with GQ-5 significantly blocked the interaction of Smad3 with TβRI, but did not affect the interaction of Smad2 with TβRI.

Example 17

GQ-5 Selectively Blocks the Interaction of Smad3 with T3RI In Vivo

1. Animal Model

Male Sprague-Dawley rats with body weight 200 to 250 g were randomized into 3 groups (n=6 in each group): (1) sham operated rats; (2) UUO rats; (3) UUO+GQ-5 rats.

2. Sample Source and Preparation

GQ-5 was dissolved in 5% propylene glycol.

(1) Sham operated rats: daily intraperitoneal injection of 5% propylene glycol;

(2) UUO rats: daily intraperitoneal injection of 5% propylene glycol;

(3) UUO+GQ-5 rats: daily intraperitoneal injection of GQ-5 (40 mg/kg body weight) right after UUO;

3. Experimental Methods

UUO was performed using an established protocol as described. GQ-5 was dissolved in 5% propylene glycol. Rats were administrated with GQ-5 as described before. All the rats were sacrificed 14 days after UUO. Immunoprecipitation analyses were performed to examine the interaction among TβRI, TβRII, Smad3 and Smad2.

4. Results

Figure 14A:
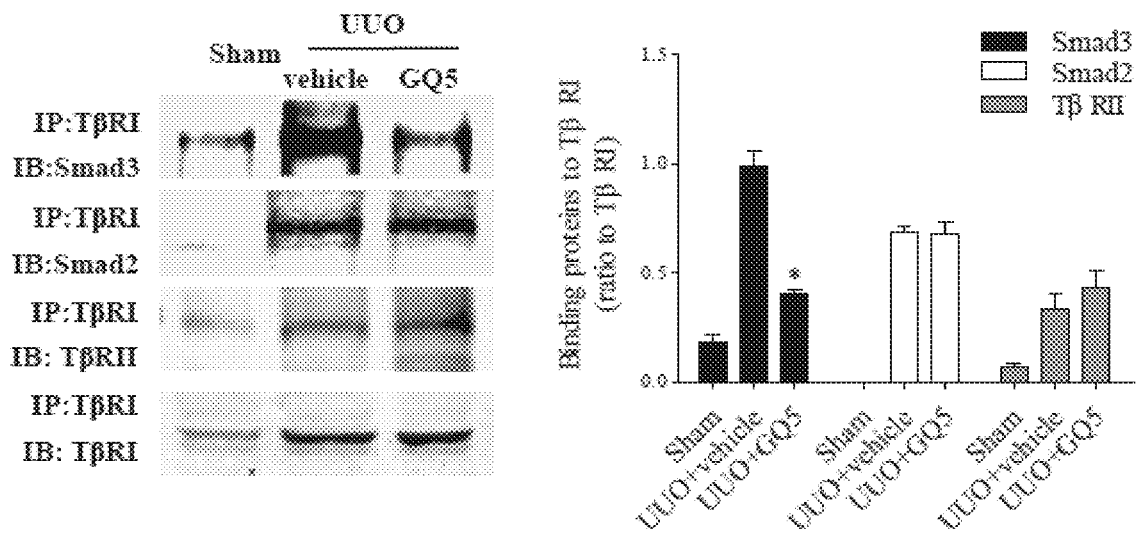
FIGS. 14A-14C illustrate GQ-5 selectively blocks the interaction of Smad3 with TβRI in UUO rats.
Figure 14B:
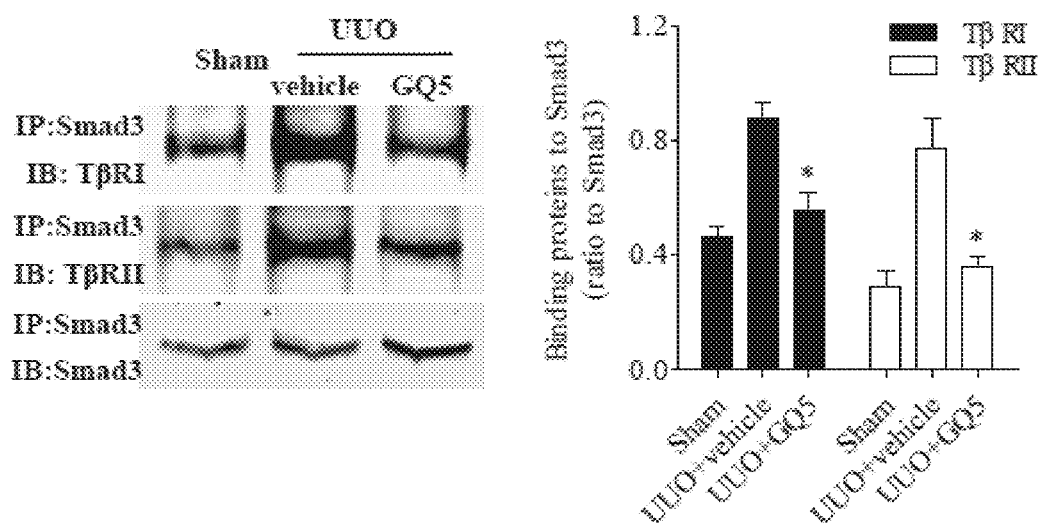
Figure 14C:
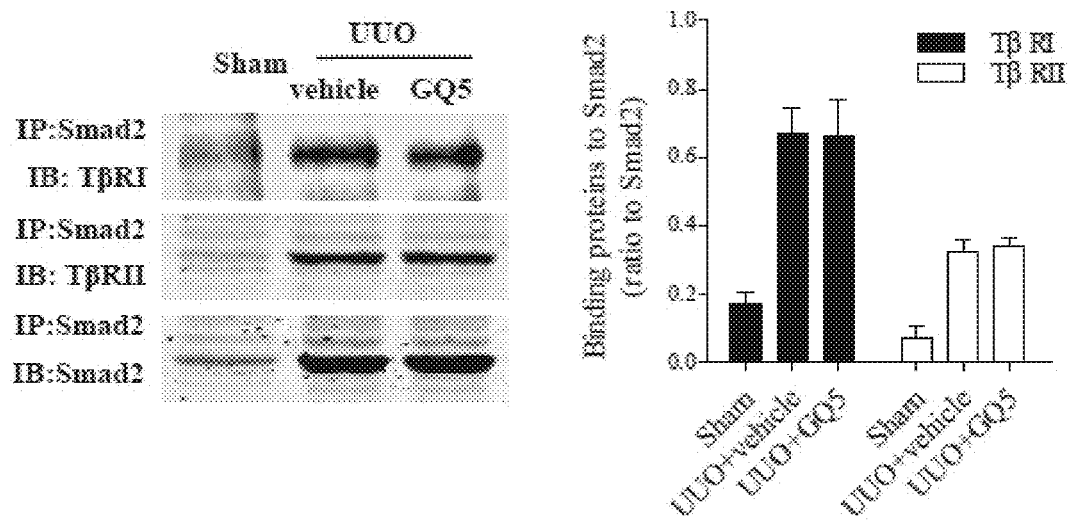

As shown in FIGS. 14A-14C, TβRI bound with TβRII, Smad2 and Smad3 in UUO kidneys. Treatment with GQ-5 significantly blocked the interaction of Smad3 with TβRI, but did not affect the interaction of Smad2 with TβRI.

In the description above, numerous specific details are set forth. However, it is understood that embodiments of the invention may be practiced without these specific details. For example, well-known equivalent components and elements may be substituted in place of those described herein, and similarly, well-known equivalent techniques may be substituted in place of the particular techniques disclosed. In other instances, well-known structures and techniques have not been shown in detail to avoid obscuring the understanding of this description.

The flowchart and block diagrams in the Figures illustrate the architecture, functionality, and operation of possible implementations of systems and methods according to various embodiments of the present invention. In this regard, each block in the flowchart or block diagrams may represent one or more modules, segments, steps, procedures, etc. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments. If the specification states a component, feature, structure, or characteristic "may," "might," or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:
1. A method for treating renal fibrosis by inhibiting Smad3 phosphorylation, comprising:
   providing an urushiol compound; and
   applying the urushiol compound as an active constituent,
   wherein the urushiol compound is dissolved in 5% propylene glycol, and
   wherein the urushiol compound is:
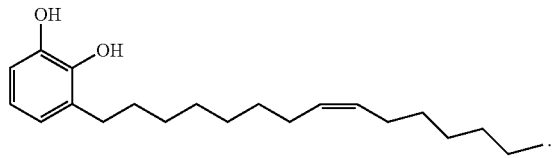 [SMILES: CCCCCC/C=C\CCCCCCCc1cccc(O)c1O]
* * * * *